(12) United States Patent
Subramanyam

(10) Patent No.: US 9,717,245 B2
(45) Date of Patent: Aug. 1, 2017

(54) TOTAL FOLIAR PRODUCT FOR AGRICULTURE / HORTICULTURE / TISSUE CULTURE AND HYDROPONIC CULTIVATION

(71) Applicant: Sundaresan Subramanyam, Chennai (IN)

(72) Inventor: Sundaresan Subramanyam, Chennai (IN)

( * ) Notice: Subject to any disclaimer, the term of this patent is extended or adjusted under 35 U.S.C. 154(b) by 0 days.

(21) Appl. No.: 14/766,245

(22) PCT Filed: Jan. 2, 2014

(86) PCT No.: PCT/IN2014/000003
§ 371 (c)(1),
(2) Date: Aug. 6, 2015

(87) PCT Pub. No.: WO2014/122669
PCT Pub. Date: Aug. 14, 2014

(65) Prior Publication Data
US 2015/0373981 A1     Dec. 31, 2015

(30) Foreign Application Priority Data
Feb. 7, 2013   (IN) .............. 522/CHE/2013

(51) Int. Cl.
| | | |
|---|---|---|
| *A01N 59/00* | (2006.01) | |
| *A01N 59/02* | (2006.01) | |
| *A01N 59/16* | (2006.01) | |
| *A01N 59/20* | (2006.01) | |
| *A01N 43/90* | (2006.01) | |
| *C05C 3/00* | (2006.01) | |
| *C05D 1/00* | (2006.01) | |
| *C05D 3/00* | (2006.01) | |
| *C05D 9/00* | (2006.01) | |
| *C05D 9/02* | (2006.01) | |
| *C05F 11/02* | (2006.01) | |
| *C05G 3/00* | (2006.01) | |
| *A01N 25/32* | (2006.01) | |

(52) U.S. Cl.
CPC .............. *A01N 43/90* (2013.01); *A01N 25/32* (2013.01); *C05C 3/00* (2013.01); *C05D 1/00* (2013.01); *C05D 3/00* (2013.01); *C05D 9/00* (2013.01); *C05D 9/02* (2013.01); *C05F 11/02* (2013.01); *C05G 3/0005* (2013.01); *C05G 3/007* (2013.01)

(58) Field of Classification Search
None
See application file for complete search history.

(56) References Cited

U.S. PATENT DOCUMENTS

| | | |
|---|---|---|
| 2,223,316 A | 11/1940 | Ellis et al. |
| 4,048,337 A | 9/1977 | Fabbian |
| 4,251,255 A | 2/1981 | Wagner et al. |
| 5,047,078 A | 9/1991 | Gill |
| 2010/0197961 A1 | 8/2010 | Giles |

FOREIGN PATENT DOCUMENTS

| | | | |
|---|---|---|---|
| EP | 1772444 | * | 4/2007 |
| WO | 8704321 A2 | | 7/1987 |
| WO | 2007042173 A2 | | 4/2007 |

OTHER PUBLICATIONS

IInternational Search Report and Written Opinion from corresponding International Application No. PCT/IN2014/000003, mailed Jun. 12, 2014, 10 pages.
"HEDP.Na2" Trade Info [online] Tongyu (China) [Online] Jan. 17, 2013. Retrieved from the Internet [retrieved on Jun. 6, 2014]:http://www.tootoo.com/s-ps/hedp-acid-hedp.na2-20-mincas-7414-83-7-c2h6o7p2na2-na2hedpa-na2hedp-etidronate-disodium-hedp--p-6812692.html.

* cited by examiner

*Primary Examiner* — Alton Pryor
(74) *Attorney, Agent, or Firm* — Innovation Capital Law Group, LLP; Vic Lin

(57) ABSTRACT

A foliar product for use in agriculture and horticulture comprising heterocyclic nitrogen source, chelating agent and metal salts. The heterocyclic nitrogen source is Hexamine. The chelating agent is disodium salt of Hydroxy Ethylidene Di Phosphonic Acid (Na2HEDP). The metal salts are chelated using the chelating agent Na2HEDP. The foliar product provides complete raw material requirement, which enables plants to synthesize various products. Further, the present invention relates to a method of manufacturing the foliar product. Advantageously, the present invention eliminates undesirable side effects in plants and helps plants survive environmental or biological stress conditions.

13 Claims, 1 Drawing Sheet

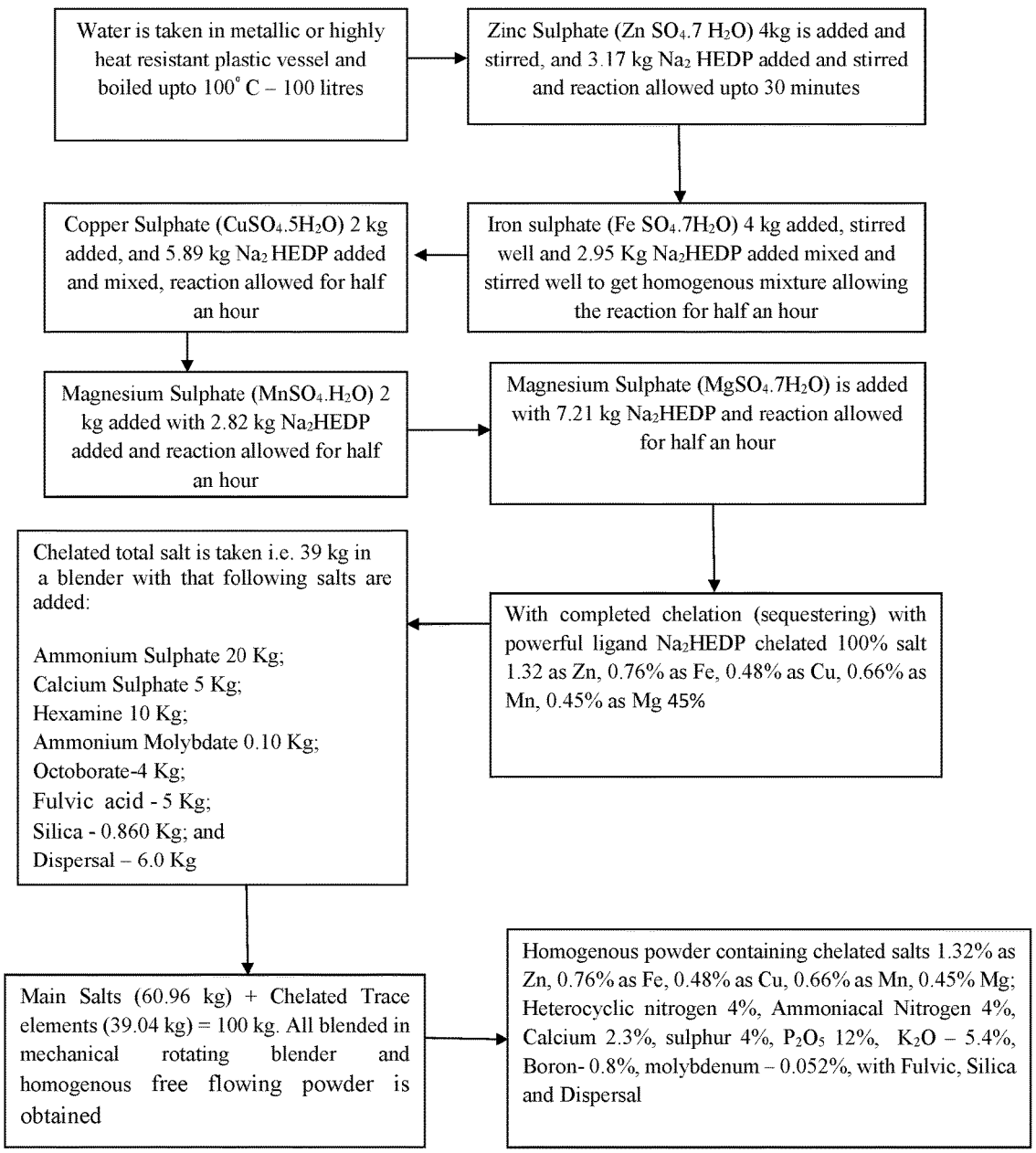

TOTAL FOLIAR PRODUCT FOR AGRICULTURE / HORTICULTURE / TISSUE CULTURE AND HYDROPONIC CULTIVATION

FIELD OF INVENTION

The present invention relates to a foliar product for use in agriculture, horticulture, tissue culture and hydroponics. More particularly, the present invention relates to a foliar product, which provides complete raw material requirement that enables plants to synthesize various products. Further, the present invention relates to a method of manufacturing the foliar product. Advantageously, the present invention eliminates undesirable side effects in plants and helps plants survive environmental or biological stress conditions.

DESCRIPTION OF PRIOR ART

Raw materials that enter the plant system help plants to synthesize products like carbohydrate, fat, protein by photosynthesis. In secondary photosynthesis, plants synthesize products like vitamins, enzymes, steroids, polysaccharides, coumarin, phenols, glycosides, brassinolides, salicylates etc numbering upto 200 and odd products in different plants.

Arid Zone crop failures, excess rain crop damage, tissue culture and hydroponic cultivation are studied to save crop loss and low yield. The World arid zone cultivable area is 2000 million hectares. Cropland accounts 20% in degrading soil and 50% of livestock is supported by dry land area only. When compared to entire cultivable area, 44% is dry land in the World. Largest dry land areas are in USA, China, Russia and Australia. In India 70 to 80% is rain fed area. Most of the rain fed area in developing countries suffers from one or the other form of land degradation. Stress conditions such as drought, salinity, dampness etc cause excess damage to plants and crops. In conditions such as drought stress, the capillary action fails from soil to plant because water is not available and during dampness, nutrients from plant enter the soil, thereby depleting the plant of its nutrients. Recurring drought in one area or the other and conditions like dampness needs a total solution.

Known in prior art are macronutrients and micronutrients such as NPK, Cu, Mn, Mg, B, Zn, Fe, Mo etc derived from conventional fertilizer to meet the plant nutrient requirements. Also known in prior art are products available separately for foliar, tissue culture and hydroponics application.

U.S. Pat. No. 5,047,078 relates to a fertilizing composition for increasing the availability of soil nutrients comprising a phosphate fertilizer and a scale-inhibiting compound.

US20100197961 discloses an adduct of 1-hydroxyethylidene-1,1-diphosphonic acid used for agricultural applications such as herbicides, foliar feeds, nutrient feeds and hydroponics.

WO8704321 discloses a method for increasing crop yield by the use of novel heterocyclic nitrogen-containing compounds.

WO2007042173 discloses granular ammonium nitrate fertilizers containing a filler composition. The filler composition contains an inorganic component and phosphonic acid compatibilizing agent.

Accordingly, there exists a need for a single composition to be used for foliar application, tissue culture and hydroponic cultivation. The present invention is designed to meet the plant nutritional requirements in a complete way.

OBJECTS OF INVENTION

The primary object of the present invention is to provide a foliar product for use in agriculture, horticulture, tissue culture and hydroponics.

It is another object of the present invention to provide a foliar product that provides complete raw material requirement, which enables plants to synthesize various products.

It is another object of the present invention to provide a method of manufacturing the foliar product.

It is another object of the present invention to provide a foliar product that eliminates undesirable side effects in plants and helps plants survive environmental or biological stress conditions such as drought, damp conditions, weedicide shock, pesticide shock, adverse climate conditions, adverse soil condition like acidity and alkalinity etc.

It is another object of the present invention, wherein the foliar product is used in simultaneous flowering and fruiting plants/crops to prevent premature flower and fruit drop.

It is another object of the present invention, wherein the foliar product helps in plant growth and increases plant yield.

It is another object of the present invention, wherein the foliar product helps to increase photosynthesis, thus minimizing competition during' peak fruiting and flowering, thereby increasing yield.

It is another object of the present invention, wherein the foliar product provides multifarious ways to safeguard agriculture and life stock production.

It is another object of the present invention, wherein metal salts (trace elements) are completely chelated and hence 100% is available to plants.

It is another object of the present invention, wherein the foliar product is in flowable powder form and is completely soluble.

It is another object of the present invention, wherein the foliar product can be used for hydroponic cultivation.

It is another object of the present invention, wherein the foliar product can be used for plant tissue culture.

SUMMARY OF INVENTION

Thus according to the basic aspect of the present invention there is provided a foliar product for use in agriculture and horticulture comprising:
Heterocyclic nitrogen source;
Chelating agent; and
Metal salts,
wherein the heterocyclic nitrogen source is Hexamine,
wherein the chelating agent is disodium salt of Hydroxy Ethylidene Di Phosphonic Acid ($Na_2HEDP$), and
wherein the metal salts are chelated using the chelating agent $Na_2HEDP$.

It is another aspect of the present invention, wherein the foliar product consists of 10% by weight of heterocyclic nitrogen.

It is another aspect of the present invention, wherein the foliar product consists of 22% by weight of chelating agent.

It is another aspect of the present invention, wherein the foliar product consists of 17% by weight of metal salts.

It is another aspect of the present invention, wherein the metal salts includes Zinc Sulphate Monohydrate (ZnSO$_4$.H$_2$O), Iron Sulphate (FeSO$_4$), Copper Sulphate (CuSO$_4$), Manganese Sulphate (MnSO$_4$) and Magnesium Sulphate (MgSO$_4$).

It is another aspect of the present invention, wherein the foliar product further comprises of Ammonium Sulphate, Calcium Silicate, Potassium Hydroxide, Octoborate, Ammonium Molybdate, Fulvic Acid, Silica, and Dispersal Agent.

It is another aspect of the present invention, wherein the foliar product consists of 20% by weight of Ammonium sulphate, 5% by weight of Calcium Silicate, 10% by weight of Potassium hydroxide, 4% by weight of Octoborate, 0.1% by weight of Ammonium Molybdate, 5% by weight of Fulvic Acid, 0.86% by weight of silica and 6% by weight of dispersal.

It is another aspect of the present invention, wherein the dispersal agent is alkyl aryl sulphate.

It is another aspect of the present invention, wherein the foliar product is in flowable powder form.

It is another aspect of the present invention, wherein the foliar product is completely soluble.

It is another aspect of the present invention, wherein the pH of the foliar product ranges between 2.5 and 3.5.

It is another aspect of the present invention, wherein the foliar product can be used for hydroponic cultivation and plant tissue culture.

In another aspect of the present invention, there is provided a process for preparing the foliar product comprising the steps of:

Dissolving a specific quantity of each of metal salts in water separately and further adding a specific quantity of chelating agent to each of the metal salt solutions;

Heating the resultant solution at a specific temperature for a specific time;

Evaporating the resultant solution to obtain powder and drying the powder;

Adding specific quantities of hexamine, ammonium sulphate, calcium silicate, potassium hydroxide, ammonium molybdate and octoborate to the dried powder and further blending;

Drying the resultant powder;

Adding specific quantities of alkyl aryl sulphate, fulvic acid and silica to the resultant dried powder; and Mixing thoroughly in blender to obtain final product.

It is another aspect of the present invention, wherein the specific temperature is 100° C.

It is another aspect of the present invention, wherein the specific time is 30 minutes.

BRIEF DESCRIPTION OF THE FLOWCHARTS

FIG. 1 is a flowchart showing the process for preparing the foliar product according to the present invention.

DETAILED DESCRIPTION OF THE INVENTION WITH REFERENCE TO ACCOMPANYING FIGURE

The present invention relates to a foliar product for use in agriculture and horticulture applications and a method of manufacturing the said foliar product. The foliar product of the present invention provides complete raw material requirement for the plants and this enables plants to synthesize various products and helps in plant growth. Additionally, the present invention helps to increase photosynthesis, thus minimizing competition during peak fruiting and flowering, thereby increasing yield. The present invention is used in simultaneous flowering and fruiting plants/crops to prevent premature flower and fruit drop. Moreover, undesirable side effects in plants are eliminated by the use of the product of the present invention and it helps plants survive environmental or biological stress conditions such as drought, damp conditions, weedicide shock, pesticide shock, adverse climate conditions, adverse soil condition like acidity and alkalinity etc. Thus, the invention provides multifarious ways to safeguard agriculture and life stock production.

The foliar product of the present invention comprises a heterocyclic nitrogen source, chelating agent and metal salts (trace elements). The source of heterocyclic nitrogen is Hexamine and the chelating agent used is disodium salt of Hydroxy Ethylidene Di Phosphonic Acid (Na$_2$HEDP). The metal salts (trace elements) are utilized in the present invention in chelated form and the chelation of the metal salt (trace element) is done using the chelating agent—disodium salt of Hydroxy Ethylidene Di Phosphonic Acid (Na$_2$HEDP), having a chelating power of 1:600. Chelation is carried out to avoid fixation and unwanted interactions. The foliar product consists of 10 kg heterocyclic nitrogen, 22 kg chelating agent and 17 kg metal salts (trace elements). The metal salts (trace elements) include Zinc. Sulphate Monohydrate (ZnSO$_4$.H$_2$O), Iron Sulphate (FeSO$_4$), Copper Sulphate (CuSO$_4$), Manganese Sulphate (MnSO$_4$), Magnesium Sulphate (MgSO$_4$). Further, ammonium sulphate, calcium silicate, potassium hydroxide, octoborate, ammonium molybdate, fulvic acid, silica, and dispersal agent forms part of the foliar product present in amounts as 20 kg of Ammonium sulphate, 5 kg of Calcium Silicate, 10 kg of Potassium hydroxide, 5 kg of Fulvic Acid, 0.86 kg of silica and 6 kg of dispersal. Octoborate and Ammonium Molybdate are present in the amounts 4 kg and 0.1 kg respectively. The dispersal agent used is alkyl aryl sulphate. Phosphorus pentoxide (P$_2$O$_5$) from chelating agent and potash from alkali potassium hydroxide (KOH) maintains derived pH of the foliar product. The pH of the foliar product is maintained between 2.5 and 3.5 and the final product obtained is in flowable powder form that is completely soluble. Additionally, the foliar product finds use in hydroponic cultivation and plant tissue culture.

The process of preparation of the foliar product as shown in flow chart 1 involves dissolving a specific quantity of the metal salt (trace element) in water and adding a specific quantity of the chelating agent to each of the metal salt solutions. Every individual chelation takes place in a time span of half an hour. The resultant mixture/solution obtained is heated at a specific temperature for a specific time. The specific temperature is 100° C. and the specific time is half an hour. Each of the metal salts (trace elements) is dissolved in water, chelated to solve the reaction problem among cation and anion and subjected to heating in a manner as above. Further, the resultant mixture/solution is evaporated to obtain powder and the powder is dried in a mechanical drier. To the dried powder specific quantities of hexamine, ammonium sulphate, calcium silicate, potassium hydroxide, ammonium molybdate and octoborate is added and further blended in a mechanical blender. The resultant powder is dried again in the mechanical drier and specific quantities of alkyl aryl sulphate, fulvic acid and silica is added and mixed thoroughly to obtain final composition. The chelation process is as shown below:

| | | | |
|---|---|---|---|
| Zinc Sulphate Monohydrate | 4 kg | 1.32% as Zn | 3.17 kg Na$_2$HEDP |

-continued

| | | | |
|---|---|---|---|
| Iron Sulphate | 4 kg | 0.76% as Fe | 2.95 kg Na$_2$HEDP |
| Copper Sulphate | 2 kg | 0.48% as Cu | 5.89 kg Na$_2$HEDP |
| Manganese Sulphate | 2 kg | 0.66% as Mn | 2.82 kg Na$_2$HEDP |
| Magnesium Sulphate | 5 kg | 0.45% as Mg | 7.21 kg Na$_2$HEDP |
| | 17 kg | | 22.04 kg |
| Na$_2$HEDP | 22.04 kg | | |
| All trace elements | 17 kg | | |

The above five metal salts in quantities as indicated against each are dissolved in water and specific quantities of the chelating agent as indicated above is added to each of the metal salts i.e. 3.17 kg Na$_2$HEDP is added to 4 kg Zinc Sulphate Monohydrate, 2.95 kg Na$_2$HEDP is added to 4 kg Iron Sulphate, 5.89 kg Na$_2$HEDP is added to 2 kg Copper Sulphate, 2.82 kg Na$_2$HEDP is added to 2 kg Manganese Sulphate and 7.21 kg Na$_2$HEDP is added to 5 kg Magnesium Sulphate.

This is boiled at 100° C. for 30 minutes and evaporated to obtain powder, which is further dried in the mechanical drier. The following compounds are added to the dried powder in quantities as indicated and further blended in mechanical blender and dried as required.

| | |
|---|---|
| Ammonium sulphate | 20 kg |
| Calcium Silicate | 5 kg |
| Hexamine | 10 kg |
| KOH | 10 kg |
| Ammonium Molybdate | 0.10 kg |
| Octoborate | 4 kg |
| Fulvic acid | 5 kg |
| Silica | 0.860 kg |
| Dispersal | 6 kg |
| | 60.96 kg |

The resultant foliar product obtained comprises the following:

| | | | |
|---|---|---|---|
| Hexamine | 10 kg | Heterocyclic Nitrogen | 4% |
| Ammonium sulphate | 20 kg | Ammoniacal Nitrogen | 4% |
| | | Sulphur | 4% |
| Calcium Silicate | 5 kg | Calcium | 2.3% |
| Na$_2$HEDP | 22 kg | Wholesome P$_2$O$_5$ | 12% |
| KOH | 10 kg | as K$_2$O | 5.4% |
| Zinc Sulphate Monohydrate | 4 kg | Chelated Zinc | 1.32% |
| Iron Sulphate | 4 kg | Chelated Iron | 0.76% |
| Copper Sulphate | 2 kg | Chelated Copper | 0.48% |
| Manganese Sulphate | 2 kg | Chelated Manganese | 0.45% |
| Magnesium Sulphate | 5 kg | Chelate Magnesium | 0.45% |
| Octoborate | 4 kg | Boron | 0.8% |
| Ammonium Molybdate | 0.1 kg | Molybdenum | 0.052% |
| Fulvic Acid | 5 kg | | |
| Silica | 0.86 kg | | |
| Dispersal | 6 kg | | |

The resultant foliar product is mixed thoroughly to get the final product in flowable powder form. The foliar product is also used for plant tissue culture and hydroponic cultivation.

The compositions of the foliar product used in plant tissue culture and hydroponic cultivation are as below:

A. Hydroponics:

For hydroponics i.e. soil less cultivation, the foliar product is used at 2 gm to 3 gm/ltr of pure water medium.

B. Tissue Culture:

Murashige and Skoog is a plant growth medium commonly used in plant tissue culture, agar is also a medium; as a medium, it can be added initially after which the product of the present invention is added. Instead of using four medium, the product of the present invention used in tissue culture for different plants/crops can be dovetailed as below:

B I. Composition I Used for Plant Tissue Culture:

| | 2.8% per litre |
|---|---|
| Murashige and Skoog | 4303.53 mg |
| Foliar product | 4100 mg |
| Sucrose | 20000 mg |
| Indole Acetic acid | 100 mg |
| Adenine Sulphate | 80 mg |
| i-Inositol | 100 mg |

B II. Composition II Used for Plant Tissue Culture:

| | 2.8% per litre |
|---|---|
| Murashige and Skoog | 4303.53 mg |
| Foliar product | 4100 mg |
| Sucrose | 20000 mg |
| Napthile Acetic acid | 0.100 mg |
| Adenine Sulphate | 40 mg |
| Thiamine HCL | 0.400 mg |
| i-Inositol | 100 mg |

The foliar product can be used in plant tissue culture in different concentrations.

Various field experiments were conducted to study the effect of foliar product according to the present invention on plants/crops. Table 1A and Table 1B shows the response of 'Allwin' foliar application and yield of soybean variety JS 93-05. The name "Allwin" herein after used refers to the foliar product of the present invention.

TABLE 1A

| Treatments | No. of flowers/ plant | Nodules/ plant | Nodule dry Wt (mg/p) | N % in nodules | Collar rot induced post emergence mortality |
|---|---|---|---|---|---|
| Ab. control | 93.6 | 41.6$^b$ | 70.3$^c$ | 0.70$^b$ | 24.8$^{ab}$ |
| RDF | 101.3 | 56.6$^{ab}$ | 89.3$^{ab}$ | 0.78$^{ab}$ | 21.7$^a$ |
| Allwin 2 g/L | 99.6 | 48.6$^{ab}$ | 69.6$^c$ | 0.75$^b$ | 27.8$^b$ |
| Allwin 3 g/L | 100.3 | 52.6$^{ab}$ | 80.3$^{bc}$ | 0.79$^{ab}$ | 24.0$^{ab}$ |
| *Rhizobium* | 104.6 | 54.6$^{ab}$ | 96.6$^a$ | 0.86$^{ab}$ | 22.4$^{ab}$ |
| *Rhizobium* + Allwin 2 g/L | 98.6 | 62.3$^{ab}$ | 71.3$^c$ | 0.83$^{ab}$ | 22.7$^{ab}$ |
| *Rhizobium* + Allwin 3 g/L | 93.3 | 64.6$^a$ | 72.6$^c$ | 0.92$^a$ | 19.8$^a$ |
| LSD (P = 0.05) | NS | 19.50 | 12.84 | 0.15 | 5.3 |

The above experiment is further developed and the product of the present invention is an improvement over the above.

TABLE 1B

| Treatments | Biomass DryWt (g/plant) | Plant Height (cm) | No of pods/plant | 100 seed weight (g) | Seed yield/plant | Grain yield Kg/ha |
|---|---|---|---|---|---|---|
| Ab.control | 7.8$^b$ | 24.4 | 12.3$^b$ | 7.9 | 1.39$^d$ | 401.6$^d$ |
| RDF | 10.2$^a$ | 26.2 | 17.0$^{ab}$ | 8.2 | 2.17$^a$ | 493.3$^a$ |
| Alllwin 2 g/L | 7.6$^b$ | 26.0 | 17.3$^a$ | 8.3 | 2.07$^a$ | 442.2$^{bc}$ |
| Allwin 3 g/L | 9.1$^{ab}$ | 24.5 | 14.0$^{ab}$ | 8.3 | 1.83$^{bc}$ | 441.4$^{bc}$ |
| Rhizobium | 8.2$^{ab}$ | 25.4 | 17.6$^a$ | 8.6 | 1.69$^c$ | 420.0$^{cd}$ |
| Rhizobium + Allwin 2 g/L | 7.3$^b$ | 25.7 | 14.6$^{ab}$ | 8.3 | 1.50$^d$ | 432.2$^{bc}$ |
| Rhizobium + Allwin 3 g/L | 7.4$^b$ | 24.2 | 17.0$^{ab}$ | 8.3 | 2.01$^{ab}$ | 458.3$^b$ |
| LSD (P = 0.05) | 1.96 | NS | 4.37 | NS | 0.18 | 21.66 |

The above experiment is further developed and the product of the present invention is an improvement over the above.

Table 2 shows the effect of Allwin top foliar fertilizer on yield and quality of Bt cotton.

TABLE 2

| Treatments | Cotton Yield (kg/ha) | Ginning % | Lint Yield (kg/ha) | Seed yield (kg/ha) | Cotton yield recovery (%) |
|---|---|---|---|---|---|
| T$_1$- RDF + 1.0 gm Allwin Top/litre of water | 1333.10 | 32.72 | 436.05 | 897.05 | 119.59 |
| T$_2$- RDF + 1.5 gm Allwin Top/litre of water | 1381.07 | 33.79 | 467.04 | 914.03 | 123.90 |
| T$_3$- RDF + 2.0 gm Allwin top/litre of water | 1396.58 | 33.92 | 475.26 | 921.32 | 125.29 |
| T$_4$- 75% RDF + 1.5 gm Allwin Top/litre of water | 1085.41 | 31.29 | 340.68 | 744.73 | 97.37 |
| T$_5$- 75% RDF + 2.0 gm Allwin Top/litre of water | 1247.28 | 32.49 | 404.84 | 842.44 | 111.89 |
| T$_6$- With Farmers Practice (RDF) Control | 1114.70 | 31.84 | 354.85 | 759.85 | |
| SE (m) | 47.36 | 0.61 | 18.90 | 31.25 | |
| CD P = (0.05) | 142.67 | NS | 56.93 | 94.14 | |
| CV % | 7.52 | 3.77 | 9.15 | 7.38 | |

The data from table-2 indicates that highest cotton yield (kg/ha) and yield of Bt cotton variety 'Bunny' was recorded with treatment T$_3$ (RDF+2.0 gm Allwin Top/liter of water) over 75% RDF+2.0 gm Allwin Top/liter of water (T$_5$), 75% RDF+1.5 gm AllwinTop/liter of water (T$_4$) and RDF (T$_6$). However, the treatment T$_3$ was at par with treatments T$_1$ and T$_2$. The seed yield of cotton, treatment T$_3$ (RDF+2.0 gm Allwin Top/liter of water) was significantly superior over T$_4$ (75% RDF+1.5 gm Allwin Top/liter of water) and T$_6$ (RDF). However, the treatment T$_3$ was at par with treatments T$_1$, T$_2$, and T$_5$. The cotton yield recovery was highest with treatment with T$_3$ (125.29%) followed by T$_2$ (123.90%), T$_1$ (119.59%) and T$_5$ (111.89%) over control. In the above experiment, 75% fertilizers gave good yield with all quality parameters. Treatment differences due to various treatments were found to be non significant in respect of quality parameter viz. ginning percentage.

Table 3 shows the effect of farmyard manure (FYM) and different doses of Allwin wonder (AW) and Allwin top (AT) on the fresh yield of spring okra (t/ha) during 2010.

TABLE 3

| Tr. No. | Treatment details | FYM(t/ha) 10 | 20 | Mean |
|---|---|---|---|---|
| T1 | RDF (100%) + Allwin Wonder 1250 g/ha - 5 DAS | 10.8 | 11.8 | 11.3 |
| T2 | RDF (100%) + Allwin Wonder 2500 g/ha - 20 DAS | 11.9 | 10.9 | 11.4 |
| T3 | RDF (100%) + Allwin Top 1.0 g/l of water - 20 DAS | 11.5 | 11.5 | 11.5 |
| T4 | RDF (100%) + Allwin Top 2.0 g/l of water - 5 DAS | 10.8 | 11.2 | 11.0 |
| T5 | RDF (100%) + Allwin Wonder 2500 g/ha - 5 DAS Plus Allwin Top 2.0 g/l of water - 60 DAS | 13.0 | 12.2 | 12.6 |
| T6 | RDF (100%) | 8.6 | 10.7 | 9.6 |
| Mean | | 11.1 | 11.4 | |
| LSD (0.05) | | FYM: 0.14, Treatments: 0.36, FYM * Treatments; 0.50 | | |

The foliar product of the present invention helps to improve yield of crops/plants.

Table 4 shows the effect of farmyard manure (FYM) and different doses of Allwin wonder (AW) and Allwin top (AT) on the fresh yield of spring okra (t/ha) during September, 2010.

TABLE 4

| | Yield |
|---|---|
| A Farmyard manure (t/ha) | |
| 10 | 9.9 |
| 20 | 10.8 |
| LSD (0.05) | 0.73 |
| B sub-treatments | |
| T$_1$- RDF (100%) + Allwin Wonder 1250 g/ha - 5 DAS | 10.3 |
| T$_2$- RDF (100%) + Allwin Wonder 2500 g/ha - 20 DAS | 10.1 |
| T$_3$- RDF (100%) + Allwin Top 1.0 g/l of water - 20 DAS | 10.5 |
| T$_4$- RDF (100%) + Allwin Top 2.0 g/l of water - 5 DAS | 10.1 |
| T$_5$- RDF (100%) + Allwin Wonder 2500 g/ha - 5 DAS Plus Allwin Top 2.0 g/l of water - 60 DAS | 11.5 |
| T6- RDF (100%) | 9.8 |
| LSD (0.05) | 0.74 |

The okra yield obtained with the application of 20 t FYM ha$^{-1}$ was significantly higher (9.1 percent) over 20 t FYM ha$^{-1}$. It is worth mentioning that during monsoon season also, application of Allwin wonder and Allwin Top resulted in significantly higher yield of okra over all other treatments with or without application of Allwin Wonder. The percent increase in okra yield with the application of both Allwin wonder and Allwin Top (T5) was 17.3 than RDF.

The present invention may be embodied in other specific forms without departing from its spirit or essential characteristics. The described embodiments are to be considered in all respects only as illustrative and not restrictive.

The details of the invention, its object and advantages explained hereinbefore is to be understood that the invention, as fully described herein is not intended to be limited by the objects mentioned herein.

I claim:

1. A foliar product for use in agriculture and horticulture comprising:
    hexamethylentetramine;
    chelating agent; and
    metal salts,
    wherein the chelating agent is disodium salt of Hydroxy Ethylidene Di Phosphonic Acid ($Na_2$ HEDP), and
    wherein the metal salts are chelated using the chelating agent $Na_2$ HEDP.

2. The foliar product according to claim 1, containing 10% by weight of the Hexamethylentetramine.

3. The foliar product according to claim 1, containing 22% by weight of the chelating agent.

4. The foliar product according to claim 1, containing 17% by weight of the metal salts.

5. The foliar product according to claim 1, wherein the metal salts includes Zinc Sulphate Monohydrate ($ZnSO_4.H_2O$), Iron Sulphate ($FeSO_4$), Copper Sulphate ($CuSO_4$), Manganese Sulphate ($MnSO_4$) and Magnesium Sulphate ($MgSO_4$).

6. The foliar product according to claim 1, further comprising of Ammonium Sulphate, Calcium Silicate, Potassium Hydroxide, Octoborate, Ammonium Molybdate, Fulvic Acid, Silica, and Dispersal agent.

7. The foliar product according to claim 6, containing 20% by weight of the Ammonium sulphate, 5% by weight of the Calcium Silicate, 10% by weight of the Potassium hydroxide, 4% by weight of the Octoborate, 0.1% by weight of the Ammonium Molybdate, 5% by weight of the Fulvic Acid, 0.86% by weight of the silica and 6% by weight of the dispersal agent.

8. The foliar product according to claim 1, further comprises a dispersal agent, wherein the dispersal agent is alkyl aryl sulphate.

9. The foliar product according to claim 1 is in flowable powder form.

10. The foliar product according to claim 1, wherein the pH of the foliar product ranges between 2.5 and 3.5.

11. A process for preparing the foliar product according to claim 1, comprising the steps of:
    dissolving 17% by weight of each of metal salts that includes Zinc Sulphate Monohydrate ($ZnSO_4.H_2O$), Iron Sulphate ($FeSO_4$), Copper Sulphate ($CuSO_4$), Manganese Sulphate ($MnSO_4$) and Magnesium Sulphate ($MgSO_4$) in water separately to form separate metal salt solutions and further adding 22% by weight of chelating agent to each of the separate metal salt solutions;
    heating the resultant separate metal salt-chelating agent solutions at a specific temperature for a specific time;
    evaporating the resultant solutions to obtain a powder and drying the powder to a dried powder;
    adding 10% by weight of Hexamethylentetramine, 20% by weight of ammonium sulphate, 5% by weight of calcium silicate, 10% by weight of potassium hydroxide, 0.1% by weight of ammonium molybdate and 4% by weight of octoborate to the dried powder and further blending to form a resultant mixed powder;
    drying the resultant mixed powder to a resultant dried powder;
    adding 6% by weight of alkyl aryl sulphate, 5% by weight of fulvic acid and 0.86% by weight of silica to the resultant dried powder; and
    mixing thoroughly in blender to obtain final product.

12. The process according to claim 11, wherein the specific temperature is 100° C.

13. The process according to claim 11, wherein the specific time is 30 minutes.

* * * * *